United States Patent
Chen

(10) Patent No.: US 10,149,496 B2
(45) Date of Patent: Dec. 11, 2018

(54) ELECTRONIC CIGARETTE CONTROLLER AND ELECTRONIC CIGARETTE

(71) Applicant: Shenzhen Smoore Technology Limited, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 767 days.

(21) Appl. No.: 14/661,566

(22) Filed: Mar. 18, 2015

(65) Prior Publication Data

US 2015/0366266 A1  Dec. 24, 2015

(30) Foreign Application Priority Data

Jun. 23, 2014 (CN) .......................... 2014 1 0284823

(51) Int. Cl.
*A24F 47/00* (2006.01)
*A61M 15/06* (2006.01)
(Continued)

(52) U.S. Cl.
CPC ........... *A24F 47/008* (2013.01); *A61M 15/06* (2013.01); *H05B 1/0244* (2013.01);
(Continued)

(58) Field of Classification Search
CPC .... H05B 1/0244; A24F 47/008; A61M 15/06; A61M 2205/13; A61M 11/042;
(Continued)

(56) References Cited

U.S. PATENT DOCUMENTS

| 6,155,268 A | 12/2000 | Takeuchi |
| 2013/0255702 A1 | 10/2013 | Griffith, Jr. et al. |

(Continued)

FOREIGN PATENT DOCUMENTS

| CN | 102940313 A | 2/2013 |
| CN | 202890465 U | 4/2013 |
| CN | 203166462 U | 8/2013 |
| CN | 103280852 A | 9/2013 |

(Continued)

OTHER PUBLICATIONS

European Search Report for European Application No. 15159777.0, dated Nov. 20, 2015.
European Search Report for European Application No. 15159783.8, dated Nov. 24, 2015.

*Primary Examiner* — Shogo Sasaki
(74) *Attorney, Agent, or Firm* — HoustonHogle LLP

(57) ABSTRACT

An electronic cigarette controller includes a control chip. The control chip includes: a smoking detecting module used for detecting a capacitance change of an external mouthpiece; a control module used for sending drive and control signals according to the smoking signal, or stopping sending drive and control signals according to the standby signal; a drive module used for receiving the drive and control signals and outputting electric current to drive the electronic cigarette to work; and a tobacco liquid detecting module used for sampling an amount value of a tobacco liquid of the electronic cigarette and determining whether the amount value of the tobacco liquid is less than a preset reference value, if yes, the control module stops sending the drive and control signals. The present disclosure describes an electronic cigarette that can detect an amount of the tobacco liquid.

11 Claims, 3 Drawing Sheets

(51) Int. Cl.
*H05B 1/02* (2006.01)
*A61M 16/00* (2006.01)
*A61M 11/04* (2006.01)

(52) U.S. Cl.
CPC ... *A61M 11/042* (2014.02); *A61M 2016/0024* (2013.01); *A61M 2205/13* (2013.01); *A61M 2205/3386* (2013.01); *A61M 2205/587* (2013.01); *A61M 2205/6018* (2013.01); *A61M 2205/8206* (2013.01)

(58) Field of Classification Search
CPC .... A61M 2205/3386; A61M 2205/587; A61M 2205/6018; A61M 2205/8206; A61M 2016/0024
See application file for complete search history.

(56) References Cited

U.S. PATENT DOCUMENTS

| | | |
|---|---|---|
| 2014/0062417 A1 | 3/2014 | Li et al. |
| 2014/0254055 A1 | 9/2014 | Xiang |
| 2017/0231281 A1* | 8/2017 | Hatton .................. A24F 47/008 131/328 |

FOREIGN PATENT DOCUMENTS

| | | |
|---|---|---|
| CN | 203368107 U | 12/2013 |
| CN | 203446536 U | 2/2014 |
| CN | 103653261 A | 3/2014 |
| EP | 2489391 A1 | 8/2012 |
| WO | 2014066730 A1 | 5/2014 |

* cited by examiner

ELECTRONIC CIGARETTE CONTROLLER AND ELECTRONIC CIGARETTE

RELATED APPLICATIONS

This application claims priority under 35 U.S.C. § 119 to Chinese Patent Application No. 201410284823.1, filed Jun. 23, 2014. The entire teachings of the above application is incorporated herein by reference.

FIELD OF THE INVENTION

The present invention relates to the field of electronic devices, and more particularly relates to an electronic cigarette controller and an electronic cigarette.

BACKGROUND OF THE INVENTION

An electronic cigarette is a kind of electronic product that powered by batteries, detects air flow movement by using an internal detecting module to determine whether the electronic cigarette is in a smoking situation, and then controls an electric current output and a work state by using a chip. A heater strip in the electronic cigarette vaporizes tobacco liquid to vapor, which is inhaled into a smoker's lungs, and simulation of smoke is exhaled by the smoker. The electronic cigarette does not contain tar and other harmful substances contained in a conventional cigarette and does not generate second-hand smoke either, thus there will be no smoke filled in or swirling in a confined space. Therefore, it is a trend that electronic cigarettes are replacing conventional cigarettes.

Although the control technology of electronic cigarette is fully developed and electronic cigarette controllers have varieties of protecting functions, the conventional electronic cigarette is unable to detect an amount value of the tobacco liquid. When the tobacco liquid decreases to a certain extent, the vaporization of the tobacco liquid may not provide enough vapors to make a smoker have smoking feelings. Meanwhile, the heater strip heats the air and generates an unpleasant smell.

SUMMARY OF THE INVENTION

It is an object of the present invention to provide an electronic cigarette controller.

An electronic cigarette controller includes a control chip, the control chip includes: a smoking detecting module used for detecting a capacitance change of an external mouthpiece. When the detected capacitance is greater than (i.e., not less than) a smoking threshold, the smoking detecting module sends a smoking signal to switch on the electronic cigarette. When the detected capacitance is less than a smoking threshold, the smoking detecting module sends a standby signal to shut down the electronic cigarette. The control chip includes a control module connected to the smoking detecting module, and used for sending drive and control signals according to the smoking signal or stopping sending drive and control signals according to the standby signal. The control chip includes a drive module connected to the control module, and used for receiving the drive and control signals and outputting electric current to drive the electronic cigarette to work. The control chip includes a tobacco liquid detecting module connected to the control module, and used for sampling an amount value of a tobacco liquid of the electronic cigarette and determining whether the amount value of the tobacco liquid is less than a preset reference value. If the amount value of the tobacco liquid is determined to be less than a preset reference value, the control module stops sending the drive and control signals.

In a preferred embodiment, the amount value of the tobacco liquid is an electric current value flowing through a pin of the tobacco liquid detecting module. The pin is used for connecting with external oil storage cotton.

In a preferred embodiment, the smoking detecting module is configured to automatically identify different external mouthpieces based on a difference, and presets four different smoking thresholds according to the difference of the external mouthpieces.

In a preferred embodiment, the four different smoking thresholds are respectively equal to 3%, 6%, 9%, and 12% of the capacitance change value of the external mouthpiece.

In a preferred embodiment, the control chip further includes a charging module, wherein an output port of the charging module is connected to the control module and the drive module respectively, wherein a charging input port of the charging module is used to connect with an external power supply to implement a charging function.

In a preferred embodiment, the charging module includes a charging voltage detecting unit and a charging control unit. The charging voltage detecting unit is used for detecting a charging voltage of an external used lithium battery in real time. The charging control unit is configured to control a charging electric current according to the charging voltage.

In a preferred embodiment, the charging module includes a multiplexing port that serves as the input port and output port of the charging module, and is used for charging and discharging power.

In a preferred embodiment, the multiplexing port is connected to a bypass filter capacitor.

In a preferred embodiment, the control chip further includes a display module connected to the control module, and the display module is used for displaying a smoking status, the amount value of the tobacco liquid, and a charging status.

In a preferred embodiment, the display module includes an indicator light.

In a preferred embodiment, the controller further includes a protecting module connected to the control module, wherein the protecting module includes a short-circuit protecting unit and an open-circuit protecting unit. When an external heater strip is short-circuited or open-circuited, the protecting module is used to send a short-circuit signal or an open-circuit signal to cause the control module to stop sending the drive and control signals.

Furthermore, it is another object to provide an electronic cigarette.

An electronic cigarette includes a mouthpiece, a heater strip, an oil storage cotton, and the above electronic cigarette controller having the control chip. The mouthpiece is connected to the smoking detecting module, the heater strip is connected to the drive module, and the oil storage cotton is connected to the tobacco liquid detecting module.

In a preferred embodiment, the mouthpiece includes a pneumatic sensor.

The above described electronic cigarette controller and electronic cigarette employ the tobacco liquid detecting module to realize a detection function of the amount of tobacco liquid. When the amount value of the tobacco liquid is less than the preset reference value, the control module stops sending drive and control signals, thus enabling the heater strip connected to the control module not to heat the air when the tobacco liquid is exhausted. Thus, the electronic cigarette does not produce an unpleasant smell.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The invention will be described in detail with the following embodiments and drawings.

Figure 1:
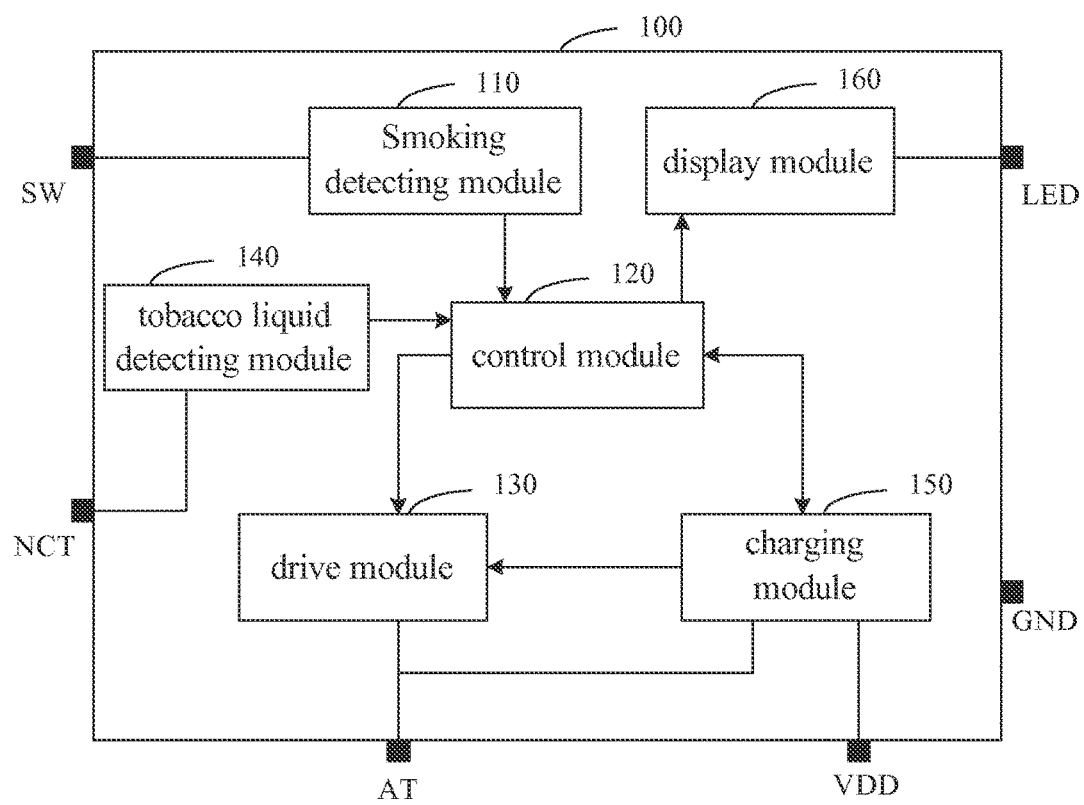
FIG. 1 is a functional block diagram of a control chip of an electronic cigarette controller according to an embodiment.

FIG. 1 is a functional block diagram of a control chip 100 of an electronic cigarette according to an embodiment. The control chip 100 includes: a smoking detecting module 110, a control module 120, a drive module 130, a tobacco liquid detecting module 140, a charging module 150 and a display module 160. The control chip 100 is in an SOT (Small Out-Line Transistor) 23-6 package form.

The control chip 100 has an SW pin serving as an input port of the smoking detecting module 110. The SW pin is used for connecting with an external mouthpiece. The smoking detecting module 110 is used for detecting a capacitance change of the external mouthpiece. When the detected capacitance is greater than (i.e., not less than) a smoking threshold, the smoking detecting module 110 sends a smoking signal to power on the electronic cigarette. When the detected capacitance is less than a smoking threshold, the smoking detecting module 110 sends a standby signal to shut down the electronic cigarette.

While under the same suction, different external mouthpieces generate different capacitance changes. In one embodiment, the smoking detecting module 110 can automatically identify different external mouthpieces. Four different smoking thresholds are preset according to the difference of external mouthpieces. The four different smoking thresholds are respectively equal to 3%, 6%, 9%, and 12% of the capacitance change value of the external mouthpiece.

The control module 120 is connected to an output port of the smoking detecting module 110. The control module 120 is used for sending drive and control signals according to the smoking signal, or stopping sending drive and control signals according to the standby signal.

An input port of the drive module 130 is connected to the control module 120. The drive module 130 is used for receiving the drive and control signals, and supplying electric current to drive the electronic cigarette to work. The input port of the drive module 130 serves as the AT pin of the control chip 100 for connecting with an external heater strip.

The control chip 100 has an NCT pin serving as an input port of the tobacco liquid detecting module 140 for connecting with an external liquid storage. The tobacco liquid detecting module 140 is connected to the control module 120. The tobacco liquid detecting module 140 is used for sampling an amount value of the tobacco liquid, then determining if the amount value of the tobacco liquid is less than a preset reference value. If yes (i.e., amount value of tobacco liquid is less than preset reference value), the control module 120 stops sending drive and control signals.

In one embodiment, the amount value of the tobacco liquid is an electric current value through the NCT pin of the control chip 100, i.e. an electric current value through the external liquid storage.

An output port of the charging module 150 is connected to the control module 120 and the drive module 130 respectively. The control chip 100 has a VDD pin serving as an input port of the charging module 150 for connecting with an external power supply to realize a charging function.

In one embodiment, a multiplexing port is employed as both the input port and output port of the charging module 150. The multiplexing port is used for charging or supplying power. Using the multiplexing port can reduce the number of pins when packaging the control chip 100, thereby decreasing the area of the system panel, and facilitating to the miniaturization of the control chip 100.

The charging module 150 includes a charging voltage detecting unit and a charging control unit connecting with each other. The charging voltage detecting unit is used for detecting charging voltage of an external lithium battery in real time. The charging control unit controls charging electric current according to the charging voltage.

In one embodiment, the charging module 150 supports charging devices such as general adapters and USB interface devices. When the charging voltage is less than 2.7 Volts, a trickle charging is performed to prevent the lithium battery from damage. When the charging voltage is larger than 2.7 Volts, a large electric current charging is performed. When the charging voltage reaches 4.2 Volts, the charging electric current gradually decreases. The charging voltage detecting unit is required to have a detecting error less than 1%.

The display module 160 is connected to the control module 120. The display module 160 is used for displaying a smoking status, an amount of tobacco liquid, and a charging status. An output port of the display module 160 serves as an LED pin of the control chip 100 for connecting with external indicator lights.

In one embodiment, the external indicator lights may indicate differently according to different application statuses. For example, while in a smoking status, the indicator lights are lit up; while in a standby status, the indicator lights are cut off; while the amount of the tobacco liquid is low, the indicator lights twinkle three times. When the battery is low, the indicator lights twinkle five times. It is easy to understand that the times of the indicator lights twinkling may be changed in other embodiments.

In addition, in other embodiments, the control chip 100 may further include a protecting module connected to the control module 120. The protecting module includes a short-circuit protecting unit and an open-circuit protecting unit. When the external heater strip is short-circuited or open-circuited, the protecting module will send a short-circuit signal or an open-circuit signal to stop the control module 120 to send drive and control signals.

The specific work principle of an electronic cigarette employing the control chip 100 in FIG. 1 is described as follows. While in a normal smoking situation, the smoking detecting module 110 can detect capacitance change of the external mouthpiece. If the capacitance value is equal to or larger than the smoking threshold, the smoking detecting module 110 sends a smoking signal to power on the electronic cigarette. The control module 120 then sends drive and control signals according to the smoking signal, making the drive module 130 output an electric current to drive the electronic cigarette to work. The indictor lights are lit on to indicate a normal smoking status. The tobacco liquid detecting module 140 starts to sample an electric current value through the external liquid storage via the NCT pin of the control chip 100. The sampled electric current value and a preset reference value are together input to an electric current comparator of the tobacco liquid detecting module 140 to be compared. When the sampled electric current value is less than the preset reference value, which means the amount of the tobacco liquid is low, the electric current comparator will output a low level voltage. The control module 120 receives an enable signal indicating the amount of tobacco liquid is low. The control module 120 stops sending drive and control signals. The control module 120 also sends a status indicating that the amount of the tobacco liquid is low to the display module 160, which then makes the indicator lights twinkle three times.

When an electric current or a voltage of the external power supply is low, the charging module 150 sends a power low signal to the display module 160 through the control module 120. The control module 120 stops sending drive and control signals.

Figure 2:
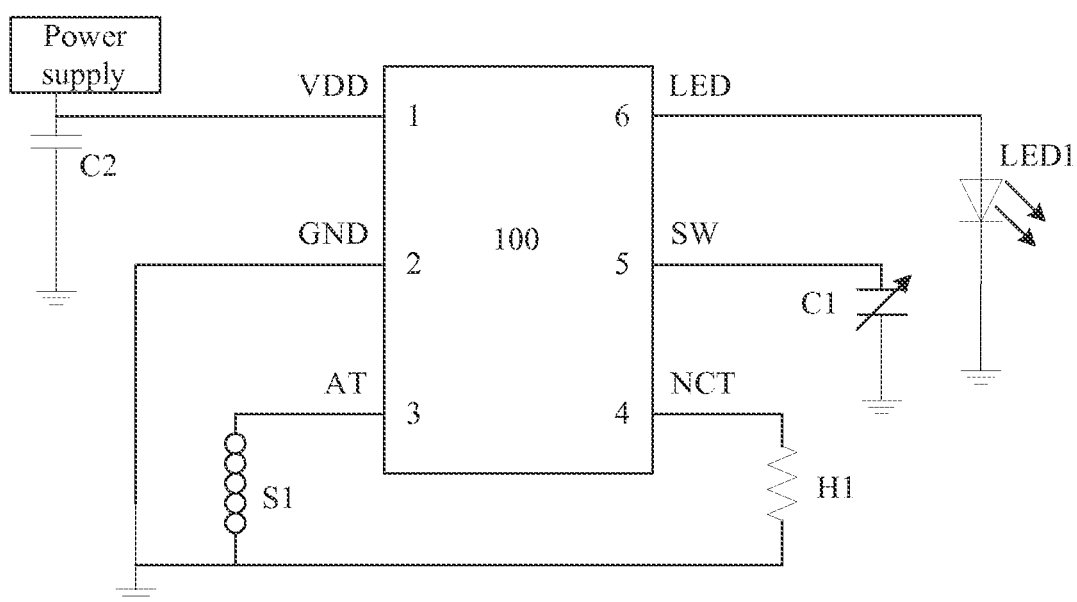
FIG. 2 is a schematic diagram of an internal structure of an electronic cigarette according to an embodiment.

As shown in FIG. 2, the present disclosure also discloses an electronic cigarette including a mouthpiece C1, a heater strip S1, a liquid storage H1, an indicator light LED1, a power supply, a capacitor C2 and the control chip 100.

The mouthpiece C1 is connected to the SW pin of the control chip 100, the heater strip S1 is connected to the AT pin of the control chip 100, the liquid storage H1 is connected to the NCT pin of the control chip 100, the indicator light LED1 is connected to the LED pin of the control chip 100. The VDD pin of the control chip 100 interconnects the positive pole of the power supply and the capacitor C2. The GND pin of the control chip 100 is grounded.

In one embodiment, the heater strip S1 is connected to an atomization device loaded with tobacco liquid. The heater strip S1 provides heat for atomization. The power supply provides power for the electronic cigarette. While in a smoking situation, vibration of the VDD pin generates impure power, which may cause logical error in the internal circuit. The capacitor C2 functions as a bypass filter to avoid the logical error.

Figure 3:
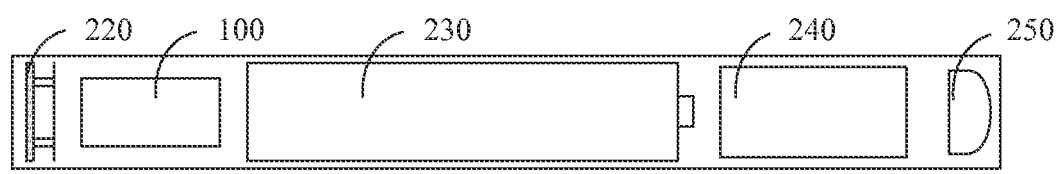
FIG. 3 is a schematic diagram of an external structure of an electronic cigarette according to an embodiment.

FIG. 3 is an external structure diagram of an electronic cigarette of an embodiment. The electronic cigarette includes the control chip 100, a pneumatic sensor 220, a battery 230, a liquid storage, a heater strip 240, and an indicator light 250. The pneumatic sensor 220 has the same function with the mouthpiece described in the above embodiment. The pneumatic sensor 220 can be deformed while detecting air flow.

By using the tobacco liquid detecting module 140, the above-described controller and electronic cigarette can detect the amount of tobacco liquid. When the amount is less than the preset reference value, the control module 120 stops sending drive and control signals, thus the heater strip 240 connected to the control module 120 stops heating the air when the tobacco liquid is exhausted, so the electronic cigarette does not produce an unpleasant smell.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An electronic cigarette, comprising:
   a mouthpiece;
   a heater strip;
   an oil storage cotton; and
   an electronic cigarette controller having a control chip, the control chip comprising:
      a smoking detecting module configured to detect a capacitance change of the mouthpiece, wherein the smoking detecting module sends a smoking signal to switch on the electronic cigarette in response to determining that the capacitance change is above a predetermined smoking threshold, and wherein the smoking detecting module sends a standby signal to shut down the electronic cigarette in response to determining that the capacitance change is below the predetermined smoking threshold;
      a control module connected to the smoking detecting module, and configured to send drive and control signals in response to receiving the smoking signal and stop sending drive and control signals in response to receiving the standby signal;
      a drive module connected to the control module, and configured to receive the drive and control signals and output electric current to drive the electronic cigarette to work based on the drive and control signals; and
      a tobacco liquid detecting module connected to the control module, and configured to sample an amount value of an electric current through the oil storage cotton and send an enable signal in response to determining that the amount value is less than a preset reference value, wherein the control module stops sending the drive and control signals in response to receiving the enable signal from the tobacco liquid detecting module;
   wherein the mouthpiece is connected to the smoking detecting module, the heater strip is connected to the drive module, and the oil storage cotton is connected to the tobacco liquid detecting module.

2. The electronic cigarette controller according to claim 1, wherein the tobacco liquid detecting module samples the amount value of an electric current flowing through a pin of the tobacco liquid detecting module, wherein the pin is configured to connect with an external oil storage cotton of the electronic cigarette.

3. The electronic cigarette controller according to claim 1, wherein the smoking detecting module is configured to automatically identify the mouthpiece of the electronic cigarette based on the detected capacitance change, and one of four different predetermined smoking thresholds is used based on the identified mouthpiece.

4. The electronic cigarette controller according to claim 3, wherein the four different smoking thresholds are respectively equal to 3%, 6%, 9%, and 12% of the detected capacitance change.

5. The electronic cigarette controller according to claim 1, wherein the control chip further comprises a charging module, wherein an output port of the charging module is connected to the control module and the drive module respectively, wherein a charging input port of the charging module is configured to connect with a power supply of the electronic cigarette for providing power to the electronic cigarette.

6. The electronic cigarette controller according to claim 5, wherein the charging module further comprises a charging voltage detecting unit and a charging control unit, the charging voltage detecting unit is configured to detect a charging voltage of an external configured lithium battery in real time, the charging control unit is configured to control a charging electric current according to the charging voltage.

7. The electronic cigarette controller according to claim 5, wherein the charging module further comprises a multiplexing port that serves as the input port and output port of the charging module, and is configured to charge and discharge power.

8. The electronic cigarette controller according to claim 7, wherein the multiplexing port is connected to a bypass filter capacitor.

9. The electronic cigarette controller according to claim 1, wherein the control chip further comprises a display module connected to the control module, and the display module is configured to cause a display of the electronic cigarette to display a smoking status, the amount value of the tobacco liquid, and a charging status based on signals from the control module.

10. The electronic cigarette controller according to claim 9, wherein the display comprises an indicator light.

11. The electronic cigarette according to claim 1, wherein the mouthpiece comprises a pneumatic sensor.

* * * * *